United States Patent
Campanale et al.

(10) Patent No.: US 8,980,231 B2
(45) Date of Patent: Mar. 17, 2015

(54) STABLE TOOTH WHITENING GEL

(75) Inventors: Joseph Campanale, Grover Beach, CA (US); William Richard Glace, Santa Maria, CA (US)

(73) Assignee: Den-Mat Holdings, LLC, Lompoc, CA (US)

( * ) Notice: Subject to any disclaimer, the term of this patent is extended or adjusted under 35 U.S.C. 154(b) by 514 days.

(21) Appl. No.: 11/729,934

(22) Filed: Mar. 30, 2007

(65) Prior Publication Data

US 2007/0253918 A1 Nov. 1, 2007

Related U.S. Application Data

(60) Provisional application No. 60/787,501, filed on Mar. 31, 2006.

(51) Int. Cl.

| | |
|---|---|
| A61K 8/22 | (2006.01) |
| A61K 8/00 | (2006.01) |
| A61Q 11/00 | (2006.01) |
| A61K 8/24 | (2006.01) |
| A61K 8/21 | (2006.01) |
| A61K 8/25 | (2006.01) |
| A61K 8/34 | (2006.01) |
| A61K 8/44 | (2006.01) |

(52) U.S. Cl.
CPC ... *A61K 8/21* (2013.01); *A61K 8/22* (2013.01); *A61K 8/24* (2013.01); *A61K 8/25* (2013.01); *A61K 8/345* (2013.01); *A61K 8/44* (2013.01); *A61Q 11/00* (2013.01)
USPC .............. 424/53; 424/49; 424/57; 424/401; 433/215; 433/216; 433/217.1

(58) Field of Classification Search
USPC ............... 424/53, 49, 401, 57; 433/215, 216, 433/217.1
See application file for complete search history.

(56) References Cited

U.S. PATENT DOCUMENTS

| | | | |
|---|---|---|---|
| 3,657,413 A | | 4/1972 | Rosenthal et al. |
| 4,117,109 A | | 9/1978 | Stookey |
| 4,226,851 A | | 10/1980 | Sompayrac |
| 4,405,599 A | | 9/1983 | Smigel |
| 4,839,157 A | | 6/1989 | Mei-King Ng et al. |
| 5,037,634 A | * | 8/1991 | Williams et al. ............... 424/49 |
| 5,098,303 A | | 3/1992 | Fischer |
| 5,234,342 A | | 8/1993 | Fischer |
| 5,374,417 A | | 12/1994 | Norfleet et al. |
| 5,376,006 A | | 12/1994 | Fischer |
| 5,599,527 A | * | 2/1997 | Hsu et al. ............... 424/52 |
| 5,725,843 A | | 3/1998 | Fischer |
| 6,106,812 A | * | 8/2000 | Prencipe et al. ............... 424/53 |
| 6,322,774 B1 | | 11/2001 | Jensen et al. |
| 6,458,340 B1 | | 10/2002 | Ibsen et al. |
| 2002/0146666 A1 | | 10/2002 | Sagel et al. |
| 2003/0091954 A1 | | 5/2003 | West et al. |
| 2003/0152528 A1 | | 8/2003 | Singh et al. |
| 2003/0198605 A1 | | 10/2003 | Montgomery |
| 2004/0109829 A1 | * | 6/2004 | Nonami et al. ............... 424/53 |
| 2004/0156796 A1 | | 8/2004 | Morgan et al. |
| 2005/0048434 A1 | | 3/2005 | Cipolla et al. |
| 2005/0084370 A1 | | 4/2005 | Gross |
| 2005/0163729 A1 | | 7/2005 | Zaidel et al. |

OTHER PUBLICATIONS

International Search Report (ISA/220 & ISA/210) dated Oct. 9, 2008 with Written Opinion (ISA/237) (Seven pages).
Tavares et al., "Light augments tooth whitening with peroxide" JADA, Feb. 2003, pp. 167-175, vol. 134.
International Search Report PCT/US07/07973, dated Oct. 8, 2008.
Haywood, V:B, et al,:, "Tray delivery of potassium nitrate-fluoride to reduce bleaching sensitivity", Feb. 2001 Quintessense Int., vol. 32, No. 2: pp. 105-109.
Gerlach, R. W., et al "Comparative response of whitening strips to a low peroxide and potassium nitrate bleaching gel", Am J Dent. Sep. 2002, 15 Spec No: 19A-23A.
Leonard, R. H., et al, "Desensitizing agent efficacy during whitening in an at-risk population", J Esthet Restor Dent, 2004, vol. 16, No. 1: pp. 49-55.
Browning, W. D et al., "Safety and efficacy of a nightguard bleaching agent containing sodium fluoride and potassium nitrate", Quintessence Int., Oct. 2004, vol. 35, No. 9, pp. 693-698.
Jorgensen, M. G., et al, "Incidence of tooth sensitivity after home whitening treatment", J Am Dent Assoc., vol. 133, No. 8, pp. 1076-1082, Aug. 2002.
Haywood, V. b., et al., "Effectiveness, side effects and long-term status of nightguard vital bleaching", J Am Dent Assoc., vol. 125, No. 9, pp. 1219-1226, Sep. 1994.
Laponite in Personal Care Products (2006).

* cited by examiner

*Primary Examiner* — Lezah Roberts
(74) *Attorney, Agent, or Firm* — Frederick W. Tong

(57) ABSTRACT

Stable tooth bleaching gels with a high concentration of peroxide are disclosed. The present invention also provides a method for treating one or more teeth. The method includes steps of applying a therapeutically effective amount of a tooth bleaching gel with a high concentration of peroxide to one or more teeth, leaving the gel in contact with the one or more teeth such that the gel may whiten the tooth or teeth.

17 Claims, No Drawings

STABLE TOOTH WHITENING GEL

This application claims priority to U.S. provisional application No. 60/787,501 filed Mar. 31, 2006.

FIELD OF THE INVENTION

The present invention relates to compositions and methods for bleaching teeth. More particularly, the present invention is directed to tooth bleaching gels having enhanced stability. White teeth have long been considered cosmetically desirable. Unfortunately, teeth almost invariably become discolored. Over time the use of certain foods and tobacco, the process of aging, diseases, trauma, medications, some congenital conditions, and environmental effects cause teeth to become discolored to varying degrees. This inevitable discoloration combined with the desire for whiter teeth have led to a high level of interest in developing compositions and methods for bleaching teeth. To this end, people have in the past relied on mechanical cleaning methods, having veneers placed over their teeth or having their teeth chemically bleached in order to achieve a desired level of tooth whiteness.

A tooth is comprised of an inner dentin layer, an outer hard, slightly porous, enamel layer and the acquired pellicle. The natural color of the tooth is opaque to translucent white or off-white. Tooth enamel is predominantly formed from inorganic material, mostly in the form of hydroxyapatite crystals and further contains approximately 5% organic material primarily in the form of collagen. The dentin layer is composed of about 20% protein, including collagen, with the balance consisting of inorganic material, predominantly hydroxyapatite crystals, similar to that found in enamel. The acquired pellicle is a proteinaceous layer on the surface of tooth enamel which reforms rapidly after an intensive tooth cleaning.

Tooth staining can generally be characterized as extrinsic or intrinsic. Staining of the acquired pellicle arises as a result of compounds such as tannins and polyphenolic compounds coming in contact with the tooth when eating, drinking or smoking. These compounds then become trapped in and tightly bound to the proteinaceous layer on the surface of the teeth. This type of staining is extrinsic. Extrinsic staining is typically removed by mechanical methods of tooth cleaning, such as brushing and/or flossing. In contrast, intrinsic staining occurs when staining compounds penetrate the enamel and even the dentin or arise from sources within the tooth. This type of staining cannot typically be addressed via mechanical methods of tooth cleaning. Chemical methods are required to remove this type of staining.

The vast majority of tooth-bleaching systems in use currently employ a form of peroxide as a whitening agent. The efficacy of peroxide compounds in oral hygiene has been long recognized. Peroxide has been used by dental clinicians for several decades as an oral antiseptic. Such compounds have proven effective in the treatment of gingivitis, oral lesions, periodontitis, and herpetic stomatitis and in combating plaque. Tooth bleaching was an observed side effect of extended contact time, thus, peroxide compounds have been utilized for oral cosmetic purposes such as tooth bleaching. The majority of tooth-whitening compounds in use currently employ carbamide peroxide ($CO(NH_2)_2H_2O_2$), also called urea hydrogen peroxide, hydrogen peroxide carbamide, and perhydrol-urea, as the whitening agent. Also, peroxide salts of the alkali or alkaline earth metals are known to be useful in bleaching teeth.

U.S. Pat. Nos. 5,098,303, 5,234,342, 5,376,006, and 5,725,843, herein incorporated by reference, teach water-based bleaching gels that contain carbomer, glycerin, and a peroxide such as hydrogen peroxide or carbamide peroxide (urea peroxide). In addition, U.S. Pat. No. 3,657,413 describes a bleaching composition that contains urea peroxide.

Further examples of tooth bleaching compositions containing peroxides can found in the disclosures of U.S. Pat. Nos. 4,839,157 and 4,405,599. These compositions included various abrasive agents such as, dicalcium phosphate, calcium carbonate, magnesium carbonate, silica or polyethylene compounds. The use of abrasive constituents in dentifrices containing peroxide compounds results irritation to both tooth and gum surfaces which is further compounded by the interaction of the peroxide composition on the abraded surfaces.

U.S. Pat. Nos. 5,098,303, 5,376,006 and 5,725,843 teach high viscosity sustained release dental compositions, such as tooth bleaching or fluoride compositions, for treating tooth surfaces. The sustained release dental compositions include a high carboxypolymethylene concentration (typically greater than 3.5%) which results in very high viscosity. The bleaching gels can contain from about 3 to about 20% carbamide peroxide, preferably about 4% to about 15% carbamide peroxide. Alternatively, the bleaching gels can contain hydrogen peroxide in a preferred range of from about 2% to about 10%.

U.S. Pat. No. 4,226,851 teaches a stable dental hygiene composition comprising a mixture of hydrogen peroxide and zinc chloride. The mixture is stabilized by the addition of water soluble vitamin E. Ultradent, produced by Ultradent Products of South Jordan, Utah, offers a 35% hydrogen peroxide bleaching gel product called Opalescence Xtra. The package contains a prominent warning which states "REFRIGERATION REQUIRED!" Similar warnings appear in two places on the package insert. Opalescence Xtra is a gel that is red in color due to the presence of .beta.-carotene. Opalescence Xtra turns into a colorless, runny liquid in less than two weeks when stored at room temperature.

None of the aforementioned references describes the stabilization of gels with respect to both gel stability and hydrogen peroxide stability. The tooth bleaching agents described above suffer from a relatively short shelf life even when refrigerated due to the collapse of the Carpapol/Glycerine gel, resulting in a product that was too fluid for use in the mouth. Thus, it would be desirable to develop a bleaching gel with a high amount of peroxide and improved stability.

The instant invention solves these stability problems by providing, for the first time, an effective bleaching gel that is stable at room temperature and that contains a large concentration of hydrogen peroxide.

SUMMARY OF THE INVENTION

This invention contemplates compositions that whiten teeth and improve overall oral hygiene.

This invention also contemplates tooth bleaching compositions that have improved stability compared to current compositions.

In one aspect, the present invention provides a composition for bleaching teeth comprising LAPONITE (sodium magnesium lithium silicate) and 0.03 micron synthetic silica.

Another aspect of the invention is directed to a composition comprising water, glycerin, LAPONITE (sodium magnesium lithium silicate), $H_2O_2$, sodium fluoride, EDTA, sodium acid pyrophosphate, flavor and microfine silica.

In a further aspect, the present invention provides a method for treating one or more teeth. The method includes steps of applying a therapeutically effective amount of a stable bleaching composition to one or more teeth, leaving the bleaching composition in contact with the one or more teeth such that the bleaching composition may whiten the tooth or teeth.

DETAILED DESCRIPTION OF THE INVENTION

For simplicity and illustrative purposes, the principles of the present invention are described by referring to various exemplary embodiments thereof. Although the preferred embodiments of the invention are particularly disclosed herein, one of ordinary skill in the art will readily recognize that the same principles are equally applicable to, and can be implicated in other compositions and methods, and that any such variation would be within such modifications that do not part from the scope of the present invention. Before explaining the disclosed embodiments of the present invention in detail, it is to be understood that the invention is not limited in its application to the details of any particular embodiment shown, since of course the invention is capable of other embodiments. The terminology used herein is for the purpose of description and not of limitation. Further, although certain methods are described with reference to certain steps that are presented herein in certain order, in many instances, these steps may be performed in any order as may be appreciated by one skilled in the art, and the methods are not limited to the particular arrangement of steps disclosed herein.

As stated, the instant invention is directed to tooth bleaching gels that contain hydrogen peroxide and that are stable at room temperature for an extended period of time. These gels may comprise: (i) a solvent; (ii) a thickening or gelling agent; (iii) bleaching agent; (iv) stabilizing agent; and, optionally, (v) neutralizing agent.

Embodiments of the invention will include at least one solvent. Examples of solvents that may be used in the invention include, but are not limited to, water, glycerin, propylene glycol, polyethylene glycol, or a variety of other compounds suitable for use as solvents for oral applications.

The gelling agent used in the present invention may present in an amount ranging from 5 to 20%. In the past, practitioners have relied on carbomer as a preferred gelling agent. The instant inventors, however, have surprisingly discovered that by replacing carbomer with a mixture of LAPONITE (sodium magnesium lithium silicate) and 0.03 micron synthetic silica the shelf life of the resulting tooth bleaching gel is significantly extended. LAPONITE (sodium magnesium lithium silicate) is highly-purified, synthetic, patented colloidal clay, which imparts viscosity and suspension properties to the gel, thereby enhancing its stability. There are many grades of LAPONITE (sodium magnesium lithium silicate) offered for applications ranging from industrial, surface coatings, agricultural, paper, household products and personal care products. The products can be divided into two general types, however: gel-forming grades and sol-forming grades. The difference between the two types is that the sol-forming grades have had tetrasodium pyrophosphate added as a dispersant to the gel-forming grades. Use of the sol-forming grades of LAPONITE (sodium magnesium lithium silicate) permit complete dispersion and incorporation of ingredients prior to gel formation. In the instant invention, gel formation is enhanced by the addition of an acid form of sodium pyrophosphate and shifts the gel's pH lower to improve the gel's peroxide stability. The present invention is not limited to the sol-forming grades: they do, however constitute the preferred embodiment.

The bleaching agent utilized in the aqueous gel is present in an amount ranging from 3 to 50%, preferably 20 to 50%, more preferably 30-40%, and most preferably 35% by weight of the aqueous gel. Higher amounts of bleaching agent are preferred so that the gel may serve as "fast acting bleaching gel" capable of bleaching teeth with only one or two applications.

The bleaching agent may be selected from hydrogen peroxide ($H_2O_2$) or any compound that yields hydrogen peroxide when placed in an aqueous medium. For example, carbamide peroxide ($CO(NH_2)_2H_2O_2$) generates hydrogen peroxide when placed in water. Other names for carbamide peroxide include urea peroxide, urea hydrogen peroxide, hydrogen peroxide carbamide, and perhydrol urea.

The stabilizing agent utilized in the aqueous gel is present in an amount ranging from 0.05 to 1% by weight of the aqueous gel. The stabilizing agent is selected from aminocarboxylic acids and salts thereof. Preferred stabilizers are selected from aminocarboxylic acids and alkali and/or alkali earth metal salts thereof. Suitable aminocarboxylic acids include trans-1,2-cyclohexylene dinitrilotetraacetic acid (CDTA), ethylenediamine tetraacetic acid (EDTA), N-(2-hydroxyethyl)ethylenediamine triacetic acid (HEDTA), Nitrilotriacetic acid (NTA), diethylene triamine pentaacetic acid (DTPA), triethylene tetraamine hexaacetic acid (TTHA), and ethyleneglycol bis(2-aminoethylether)tetraacetic acid (GEDTA). The most preferred stabilizers include CDTA, $CaNa_2$ EDTA, $Na_2$ EDTA, $Na_4$ EDTA, HEDTA, and $Na_3$ HEDTA.

The combination of the above ingredients provides a gel with a high concentration of hydrogen peroxide and that maintains the integrity of the gel for extended periods of time at room temperature. In addition, there is a reduction in hydrogen peroxide decomposition at room temperature.

A neutralizing agent, such as a hydroxide, for example, potassium hydroxide, sodium hydroxide, or ammonium hydroxide, may also be added to the gel of the instant invention. Another suitable neutralizing agent is triethanolamine. The neutralizing agent is such that it helps provide a suitable pH for the overall composition. The neutralizing agent may also serve to cross-link the thickening agent to form a suitable gel.

It may also be desirable to include other ingredients in the composition of the present invention. Such ingredients may include a flavor enhancing agent such as peppermint or spearmint oil, or any other flavor agent known in the art. Other ingredients may also include a sweetener such as saccharin or sodium saccharin or any other known sweetener. In addition to the previously mentioned ingredients, the composition of the present invention may include a solubilizing or emulsifying agent. Such agents include any known solubilizing agent suitable for oral applications.

The end result is that the aqueous gels can now be produced that have commercially viable shelf-lives at room temperature. Thus, constant refrigeration, which is both expensive and inconvenient, is no longer necessary.

The stable gel compositions of this invention may comprise, e.g., 5-10 wt % water; 5-10 wt % glycerin; 1-5 wt % LAPONITE (sodium magnesium lithium silicate); 65-75 wt % 50% hydrogen peroxide; 0-5 wt % sodium fluoride; 0-1 wt % EDTA; 0-5 wt % sodium acid pyrophosphate; 0-5 wt % flavor enhancing agent; 0-10 wt % microfine silica.

The dental bleaching gel of the instant invention can be applied to the teeth in a number of ways. In example, the gel can be applied to the teeth using a brush, syringe, tray, or any other application means.

In a typical treatment process, the soft tissues surrounding the teeth are first covered with a protecting device., e.g. a ligated rubber dam or polymerized dental resin such as Paint-On_Dental Dam (Den-Mat Corp, Santa, Maria, Calif.). This is important because the more hydrogen peroxide a dental bleaching get contains, the more likely it is to burn the soft tissue upon contact. Dental bleaching gels containing at least 30% by weight hydrogen peroxide will immediately burn and soft tissue they contact, quickly turning the tissue white. Next a brush, needle of some other delivery system is utilized to place the dental bleaching gel described above in contact with the teeth one wishes to bleach. Most patients only request treatment on the labial surfaces of the 6 to 8 front teeth which show most prominently when one smiles. The dental bleaching get is then allowed to remain in contact with the teeth for a period of time ranging anywhere from 5 minutes to one hour. One of skill in the art will recognize that the bleaching effect of any dental bleaching gel is directly proportional to this residence in time.

The bleaching effect of the hydrogen peroxide in a given period of time may be amplified by applying a heat lamp or laser light to the dental bleaching gel once it is in place on the teeth. The heat and light serve to increase the rate of bleaching of the hydrogen peroxide, providing a shorter period of time for bleaching the teeth. Upon completion of the treatment, the gel is removed with gauze or some other means. The patient's mouth is then thoroughly cleaned with water and suction.

Example 1

One embodiment of the invention may be a stable gel composition suitable for application directly to the one or more teeth to be treated. A suitable bleaching composition may have the following ingredients:

| INGREDIENT | wt % |
| --- | --- |
| Water | 7.833 |
| Glycerin | 7.833 |
| LAPONITE (sodium magnesium lithium silicate) | 3.00 |
| 50% $H_2O_2$ | 71.988 |
| Sodium Fluoride | 1.100 |
| EDTA | 0.665 |
| Sodium acid pyrophosphate | 2.000 |
| Flavor | 1.100 |
| Microfine silica | 4.483 |

Example 2

The steps below describe one aspect of the instant invention.
1. Prophy teeth to remove calculus and extrinsic stains before beginning the bleaching treatment.
2. Take "before" photographs and record tooth color using a shade guide arranged in bleaching order.
3. Insert cheek retractors. Have the patient bite down and rest tongue on a tongue block.
4. Air-dry the gingival tissue and teeth.
5. Using the dispensing tip or disposable brush, apply Den-Mat® Paint-On Dental Dam to the gingiva to isolate gums around the selected teeth. Overlap the dental dam onto the gingival tissue of adjacent teeth about 0.5 mm and light-cure for 1-2 seconds per tip width with a Sapphire™ Power Arc Curing (PAC) Light.
6. Once the Paint-On Dental Dam has been cured, apply Den-Mat Moisturizing Gel to the lips and mucosa, applying well beyond the vermillion border.
7. Remove the tip from the end of the Sapphire Desensitizer recappable syringe and dispense the Desensitizer in a very thin (about 0.5 mm) layer on the labial surface of the teeth. Distribute the gel evenly using the brush applicator provided in the kit. Firmly recap the Desensitizer syringe.
8. Immediately remove the tip from the Sapphire Whitening syringe and apply a 1-1.5 mm layer directly onto the labial surface of the teeth. Use the brush applicator to distribute the gel evenly over the teeth treated in Step 7 with the Sapphire Desensitizer Gel. Monitor the patient's comfort. Allow the treatment to remain on the patient's teeth for twenty (20) minutes, adding additional gel if needed. Place the cap back on the syringe tip to protect remaining contents.
9. At the end of the twenty minute session, vacuum gel from the teeth, wipe with gauze and rinse the teeth while suctioning. Avoid splatter.
10. Peel away the Dental Dam and evaluate the results with the patient. Some patients with heavy discoloration or areas of unseen hypocalcification may need a second 20-minute session to achieve desired bleaching results. If a second session is indicated, allow approximately five (5) minutes before resuming the treatment beginning with Step 3.
11. Use a shade guide arranged in bleaching order to compare the color of the whitened teeth to the original shade recorded in Step 2 and take 'after' photographs.

While the invention has been described with reference to certain exemplary embodiments thereof, those skilled in the art may make various modifications to the described embodiments of the invention without departing from the scope of the invention. The terms and descriptions used herein are set forth by way of illustration only and are not meant as limitations. In particular, although the present invention has been described by way of examples, a variety of compositions and methods would practice the inventive concepts described herein. Although the invention has been described and disclosed in various terms and certain embodiments, the scope of the invention is not intended to be, nor should it be deemed to be, limited thereby and such other modifications or embodiments as may be suggested by the teachings herein are particularly reserved, especially as they fall within the breadth and scope of the claims here appended. Those skilled in the art will recognize that these and other variations are possible within the scope of the invention as defined in the following claims and their equivalents.

What is claimed is:
1. A stable dental whitening composition comprising:
   a solvent;
   an inorganic gelling agent comprised of sodium magnesium lithium silicate and 0.03 micron synthetic silica;
   sodium acid pyrophosphate;
   a bleaching agent; and
   a stabilizing agent,
   wherein said stable dental whitening composition is one component.
2. The composition of claim 1, wherein the solvent comprises at least one element selected from the group consisting of: water, glycerin, propylene glycol, and polyethylene glycol.
3. The composition of claim 1, wherein the bleaching agent comprises a peroxide.
4. The composition of claim 3, wherein the bleaching agent comprises at least one element selected from the group consisting of: hydrogen peroxide and carbamide peroxide.
5. The composition of claim 1, wherein the stabilizing agent comprises at least one element selected from the group consisting of: aminocarboxylic acids and aminocarboxylic acid salts.

6. The composition of claim 5, wherein the stabilizing agent comprises at least one element from the group consisting of: aminocarboxylic acids, alkali metal aminocarboxylic acid salts, and alkaline earth metal aminocarboxylic acid salts.

7. The composition of claim 6, wherein the stabilizing agent comprises at least one element selected from the group consisting of trans-1,2-cyclohexylene dinitrilotetraacetic acid (CDTA), ethylenediamine tetraacetic acid (EDTA), N-(2-hydroxyethyl)ethylenediamine triacetic acid (HEDTA), nitrilotriacetic acid (NTA), diethylene triamine pentaacetic acid (DTPA), triethylene tetraamine hexaacetic acid (TTHA), ethyleneglycol bis(2-aminoethylether)tetraacetic acid (GEDTA) and alkali metal and alkaline metal salts thereof.

8. The composition of claim 7, wherein the stabilizing agent comprises at least one element selected from the group consisting of: CDTA, $CaNa_2EDTA$, $Na_4EDTA$, HEDTA and $Na_3HEDTA$.

9. The composition of claim 1, wherein the gelling agent is present in an amount of between 5 and 20 wt %.

10. The composition of claim 1, wherein the bleaching agent is present in an amount of between 3 and 50 wt %.

11. The composition of claim 10, wherein the bleaching agent is present in an amount of between 20 and 50 wt %.

12. The composition of claim 11, wherein the bleaching agent is present in an amount of between 30 and 40 wt %.

13. The composition of claim 12, wherein the bleaching agent is present in an amount of 35 wt %.

14. The composition of claim 1, wherein the stabilizing agent is present in an amount of between 0.05 and 1 wt %.

15. The composition of claim 1, further comprising at least one of the elements selected from the group consisting of: flavor enhancing agents, sweeteners, and solubilizing agents.

16. A stable dental whitening composition comprising:
a solvent;
a bleaching agent;
a stabilizing agent; and
up to 5 wt % sodium acid pyrophosphate;
an inorganic gelling agent comprising up to 10 wt % microfine silica and up to 5 wt % sodium magnesium lithium silicate;
wherein said stable dental whitening composition is a single component composition.

17. A stable dental whitening composition comprising:
a solvent;
a bleaching agent;
a stabilizing agent;
sodium acid pyrophosphate; and
5-20 wt % of an inorganic gelling agent comprising microfine silica and sodium magnesium lithium silicate;
wherein said stable dental whitening composition is a single component composition.

* * * * *